US008904044B2

United States Patent
Ebling et al.

(10) Patent No.: US 8,904,044 B2
(45) Date of Patent: Dec. 2, 2014

(54) ADAPTING COMPRESSION TECHNIQUES OVER DATA BASED ON CONTEXT

(75) Inventors: Maria Rene Ebling, White Plains, NY (US); William Francis Jerome, Baldwin Place, NY (US); Archan Misra, Bridgewater, NJ (US); Iqbal Mohomed, North York (CA)

(73) Assignee: International Business Machines Corporation, Armonk, NY (US)

( * ) Notice: Subject to any disclaimer, the term of this patent is extended or adjusted under 35 U.S.C. 154(b) by 1239 days.

(21) Appl. No.: 11/863,689

(22) Filed: Sep. 28, 2007

(65) Prior Publication Data

US 2009/0089446 A1   Apr. 2, 2009

(51) Int. Cl.
*G06F 15/16* (2006.01)
*A61B 5/00* (2006.01)
*H04L 29/06* (2006.01)

(52) U.S. Cl.
CPC .............. *G06F 15/16* (2013.01); *A61B 5/0022* (2013.01); *A61B 5/002* (2013.01); *H04L 69/04* (2013.01)
USPC .......................................... 709/247; 600/300

(58) Field of Classification Search
CPC .. H04N 19/00121; H04L 69/04; H04L 47/38; H04L 47/822; A61B 5/002; A61B 5/0022; A61B 5/02055; A61B 5/14532; A61B 5/222
USPC ................... 709/230, 247; 600/300
See application file for complete search history.

(56) References Cited

U.S. PATENT DOCUMENTS 6,041,044 A  *  3/2000  Seiffert et al. ................ 370/254
6,044,180 A      3/2000  Brandestini et al.
6,148,328 A     11/2000  Cuomo et al.
(Continued)

FOREIGN PATENT DOCUMENTS

| EP | 0914004 | 5/1999 |
| EP | 1263235 | 12/2002 |
| JP | 2006333446 A | 12/2006 |
| WO | WO2004034331 | 4/2004 |

OTHER PUBLICATIONS

J. Rosenberg, "Extensible Markup Language (XML) Formats for Representing Resource Lists," RFC 4826, Network Working Group, Standards Track, May 2007, pp. 1-31.

(Continued)

*Primary Examiner* — Rupal Dharia
*Assistant Examiner* — Joe Chacko
(74) *Attorney, Agent, or Firm* — Preston J Young; Ryan, Mason & Lewis, LLP

(57) ABSTRACT

Techniques for selecting a new compression technique or altering the currently instantiated compression technique employed over a data stream in data collection system are provided. At least one change to at least one external contextual condition is detected. One or more modifications to a defined compression technique is generated, either independently or in conjunction with one or more modifications to the event processing operators that operate on the data stream and whose output provides the values that are compressed by the defined compression technique, in response to the at least one change to the at least one external contextual condition. The defined compression technique of the at least one client device is altered in accordance with the one or more modifications to form a modified compression technique through which the unmodified or processed data stream will be compressed before being sent to the server.

19 Claims, 3 Drawing Sheets

(56) References Cited

U.S. PATENT DOCUMENTS

| | | | |
|---|---|---|---|
| 6,651,050 B2 | 11/2003 | Shafrir et al. | |
| 6,711,296 B1* | 3/2004 | Higuchi et al. | 382/239 |
| 6,822,945 B2 | 11/2004 | Petrovykh | |
| 6,888,893 B2* | 5/2005 | Li et al. | 375/240.25 |
| 6,898,565 B2 | 5/2005 | Bubb | |
| 7,133,561 B2 | 11/2006 | Wang | |
| 7,420,992 B1* | 9/2008 | Fang et al. | 370/477 |
| 7,469,384 B2 | 12/2008 | Thompson et al. | |
| 2001/0008556 A1* | 7/2001 | Bauer et al. | 379/265.06 |
| 2002/0055924 A1* | 5/2002 | Liming | 707/100 |
| 2002/0176629 A1* | 11/2002 | Labelle | 382/232 |
| 2003/0217098 A1 | 11/2003 | Bobde et al. | |
| 2004/0133081 A1* | 7/2004 | Teller et al. | 600/300 |
| 2005/0063472 A1 | 3/2005 | Vella et al. | |
| 2005/0175021 A1 | 8/2005 | Ozugur et al. | |
| 2005/0233776 A1 | 10/2005 | Allen et al. | |
| 2005/0235038 A1 | 10/2005 | Donatella et al. | |
| 2006/0153423 A1* | 7/2006 | Collins | 382/100 |
| 2006/0173936 A1 | 8/2006 | Castro et al. | |
| 2007/0038723 A1 | 2/2007 | Gourraud | |
| 2007/0055577 A1 | 3/2007 | Ashton | |
| 2007/0124158 A1 | 5/2007 | Kakuta et al. | |
| 2007/0177558 A1 | 8/2007 | Ayachitula et al. | |
| 2007/0213603 A1* | 9/2007 | Brown | 600/300 |
| 2008/0133644 A1 | 6/2008 | Garcia-Martin et al. | |
| 2008/0253330 A1* | 10/2008 | Bartlett | 370/331 |

OTHER PUBLICATIONS

A.B. Roach et al., "A Session Initiation Protocol (SIP) Event Notification Extension for Resource Lists," RFC 4662, Network Working Group, Standards Track, Aug. 2006, pp. 1-39.

O. Jorns et al., "A Privacy Enhancing Mechanism based on Pseudonyms for Identity Protection in Location-Based Services," Australian Computer Society, Proceedings of the fifth Australasian Symposium on ACSW frontiers, 2007, pp. 133-142, vol. 68.

V. Gehlot et al., "A Formalized and Validated Executable Model of the SIP-Based Presence Protocol for Mobile Applications," ACMSE, Mar. 2007, pp. 185-190, North Carolina.

L. Bartram et al., "Designing Portable Collaborative Networks," Colligo Networks, ACMQUEUE, May 2003, pp. 41-49, Vol, 1, No. 3.

E. Belinsky et al., "PASTA: Deriving Rich Presence for Converged Telecommunications Network Applications," IEEE, Comsware, 2007, 12 pages.

J. Rosenberg et al., "SIP: Session Initiation Protocol," RFC 3261, IETF Standards Track, Jun. 2002, pp. 1-269.

J. Rosenberg et al., A Presence Event Package for the Session Initiation Protocol (SIP), RFC 3856, IETF Standards Track, Aug. 2004, pp. 1-27.

* cited by examiner

ADAPTING COMPRESSION TECHNIQUES OVER DATA BASED ON CONTEXT

FIELD OF THE INVENTION

The present invention relates to the field of information gathering and transmission, and more particularly, to techniques for dynamically altering and modifying the compression technique and event filtering applied jointly to data streams based on some change in external context.

BACKGROUND OF THE INVENTION

Many new computing applications involve the generation and transmission of data from a group of sensor devices to a remote "sink" node, where such data is aggregated and analyzed. Such applications are becoming common in a variety of remote monitoring scenarios, such as healthcare (where wearable sensors record and transmit various biometric measures of an individual), vehicular telematics (where on-board sensors measure various vehicular parameters and transmit them back to a central diagnostic server) and intelligent transportation systems (where highway sensors periodically record traffic conditions).

Such data gathering systems have two important goals or concerns. First, as many of these sensor devices are resource-constrained themselves (e.g., operate on batteries), the system should minimize the communication and/or the data collection overhead, helping to reduce the energy expenditure or network bandwidth consumption of such devices. Second, many of these devices are not just reporting nodes, but also possess a fair degree of processing power and local intelligence. Architecturally, such data collection systems comprise a set of client sensor devices that are connected (typically using a short-range wireless technology such as Bluetooth or ZigBee) to a personal gateway device, with the gateway device subsequently being connected (often using a wireless communications infrastructure) to a remote sink node (or server), wherein this sink node is a part of an existing information technology infrastructure.

One simple form of improving the efficiency of the data gathering system is to compress the sensor data prior to transmission. Another important technique for improving the efficiency of the data transmission is to perform data filtering—this refers to the idea that much of the data may be eliminated or reduced if it is not necessary to the end goals of the infrastructure. There are a wide variety of compression schemes available—such as Huffman, Vector Quantization (VQ), Lempel-Ziv (LZ), run-length coding etc.—and can be broadly classified into two categories—lossless (where the exact data values can be recovered during decompression) and lossy (where the compressed data cannot be inverted to recover the exact data values). In general, different compression algorithms are applicable to specific types of data sources—different data sources possess different "statistical parameters" and different algorithms work better for different families of statistics. In addition, the choice of a compression algorithm is also determined by the application's requirement on the quality of the compression—e.g. does the compression need to be lossless, or can some distortion during the compression process be tolerated by the application? Similarly, the type of filtering performed directly affects the statistics of the filtered data, and thus determines the efficacy of various compression algorithms.

In many applications, the quality of the compression required is not constant for a given type of sensor data, but may vary based on some external context. Here, context refers to various dynamic attributes of the environment, such as the current location of the individual wearing the sensors, the type of activity the user is currently performing or the specific queries that the application must answer on the sensed data. As an example from remote healthcare monitoring, an application may need to retrieve the exact ECG data (i.e., permit only lossless compression) when the user is in the gym, but may only need lower-quality (lossy) data (e.g., for simple arrhythmia alerts) when the user is at home. Similarly, different forms of filtering may alter the statistics of the data associated with a sensor at different times. For example, the infrastructure may wish to be notified of the exact heart rate samples if the readings lie outside (70,90) when at home, and may require only a per-10 minute notification in case the readings lie in the range. In this case, the relaying device or sensor may perform averaging when all readings lie within this range—it stands to reason that the statistical properties of the "average" readings (e.g., their resolution, their likely variation across consecutive samples) will have very different statistics than the raw data.

It would be desirable for the system to allow the sensor devices or any relaying device the capability to dynamically modify the compression technique applied to a raw or filtered data stream based on changes to the external context.

SUMMARY OF THE INVENTION

Principles of the present invention provide techniques for dynamically altering the compression algorithms or adapting their parameters, in isolation or in conjunction with changes to the processing applied by a personal gateway device on the sensor streams, whenever there is a pertinent change in one or more external contextual parameters.

For example, in one aspect of the invention, a method for modifying a compression technique employed over a data stream in the data collection system is provided. At least one change to at least one external contextual condition is detected. One or more modifications to a defined compression technique, including the replacement of an existing compression technique with an alternative compression technique, is generated in response to the at least one change to the at least one external contextual condition. The defined compression technique of the at least one client device is altered in accordance with the one or more modifications to form a modified compression technique through which the data stream will be compressed before being sent to the server. The defined compression technique may also be modified jointly with corresponding modifications to one or more stream event processing steps, generated in response to the at least one change to the at least one external contextual condition.

In additional embodiments of the present invention, the at least one external contextual condition may be detected at a server of the data collection system, and the one or more modifications may be generated at the server of the data collection system. Further, the modifications may be transmitted from the server to the at least one client device of the data collection system.

Additionally, the data stream may be compressed in accordance with the modified compression technique at the at least one client device, and transmitted from the at least one client device to the server, wherein the compressing and transmitting steps are performed after the step of altering the defined compression technique of the at least one client device.

Another aspect of the invention is that the external change in context may refer to both changes in the operating environment of the sensor and personal gateway device, or changes in some external attributes not directly detectable by the sensors or personal gateway but retrieved by the backend infrastructure from some external context service. Examples of directly detectable attributes may include the values or pattern in the sensor event streams or the resource levels (e.g., battery level) on the personal gateway device. Examples of non-directly detectable attributes may include the medical conditions or abnormalities suspected in the user of the personal gateway device.

In another aspect of the present invention an apparatus is provided for modifying a compression technique employed over a data stream in data collection system. The apparatus comprises a memory and at least one processor coupled to the memory. The processor is operative to: (i) detect at least one change to at least one external contextual condition of the data collection system, (ii) generate one or more modifications to a defined compression technique in response to the at least one change to the at least one external contextual condition, and (iii) transmit the one or more modifications to at least one client device of the data collection system.

A second apparatus is provided in an additional aspect of the present invention for modifying a compression technique employed over a data stream in data collection system. The apparatus comprises a memory and at least one processor coupled to the memory. The processor is operative to: (i) receive one or more modifications from a server of the data collection system; and (ii) alter a defined compression technique in accordance with the one or more modifications to form a modified compression technique through which the data stream will be compressed before being sent to the server.

These and other objects, features and advantages of the present invention will become apparent from the following detailed description of illustrative embodiments thereof, which is to be read in connection with the accompanying drawings.

DETAILED DESCRIPTION OF PREFERRED EMBODIMENTS

The present invention relates to the field of information gathering and transmission in a cyber-physical environment, where sensors generate streams of data samples and an intermediate processing element is responsible for filtering or compressing the stream of data samples prior to transmission to a backend infrastructure. More particularly, the invention relates to techniques for dynamically modifying the compression technique applied independently or jointly on one or more sensor streams, based on some change in external context, which implicitly alters the quality or type of compression that the infrastructure desires on the sensor streams.

It is to be understood that while the present invention will be described below in the context of a healthcare environment, the invention is not so limited. Rather, the invention is more generally applicable to any environment in which it would be desirable to alter the compressed transmission of data generated by a sensor based on changes in external context. As used herein, the term "context" is generally understood to refer to information about the physical or virtual environment of the user and/or sensor devices and communication devices being used by the user.

It is to be appreciated that the phrase "client device" (or simply "client"), as illustratively used herein, may refer to a combination of one or more sensor devices and an intermediate gateway device acting as a client device on behalf of one or more directly connected sensor devices (as illustrated and described below in the context of FIG. 1). While the sensors and gateway may be separate devices, they may alternatively be combined into a single device. It will be evident, in the illustrative descriptions below, when the description is referring to a sensor or a gateway. However, at times, for ease of description, the sensor or the gateway, alone, may be generally referred to as a client or client device.

Figure 1:
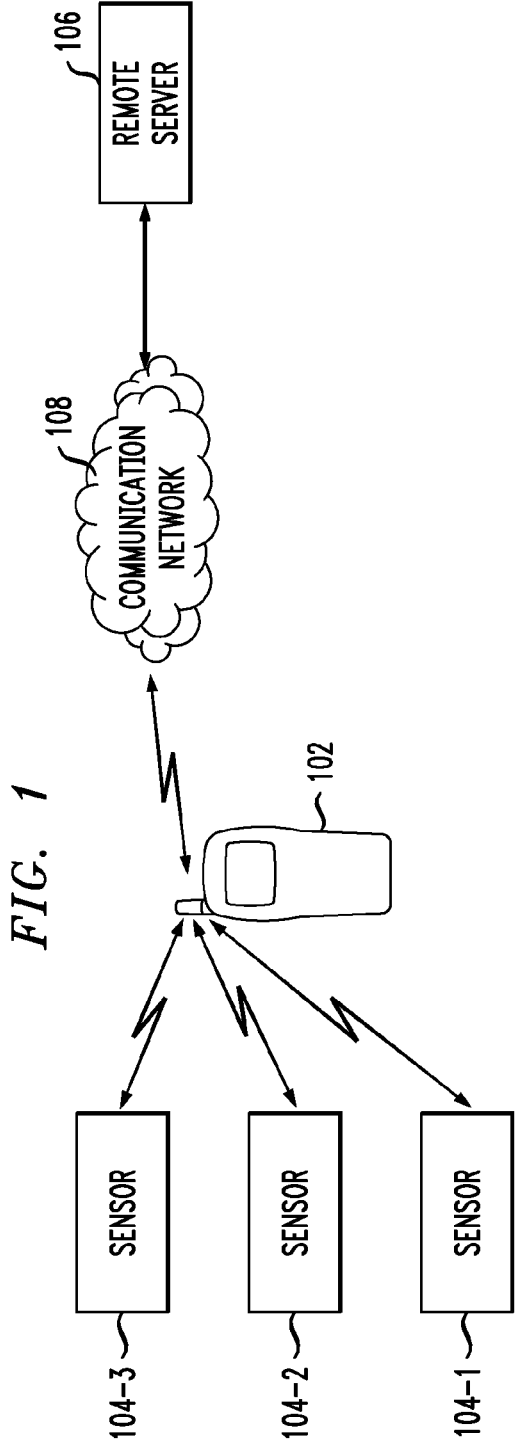
FIG. 1 is a diagram illustrating a data collection system, according to an embodiment of the present invention.

FIG. 1 illustrates a data collection system, according to an embodiment of the present invention. As shown, system 100 includes aggregation gateway 102, which is in communication with a plurality of sensors 104-1, 104-2, 104-3. In this embodiment, aggregation gateway 102 is a cell phone; however, other types and quantities of gateways may be employed. Further, more or less sensors can be employed. The plurality of sensors 104-1, 104-2, 104-3 is in communication with aggregation gateway 102 via short-range Bluetooth links 103. In accordance with the healthcare scenario, at least one of the sensors may be a health monitor which monitors some health characteristic of the user or wearer, such as, for example, heart rate, glucose level, etc. In this generic architecture, aggregation gateway 102 is known as a client device. It is to be understood that the system can include more clients. However, for simplicity, only one client is shown. Aggregation gateway 102 is in communication with a remote server 106 through a communication network 108.

Figure 2:
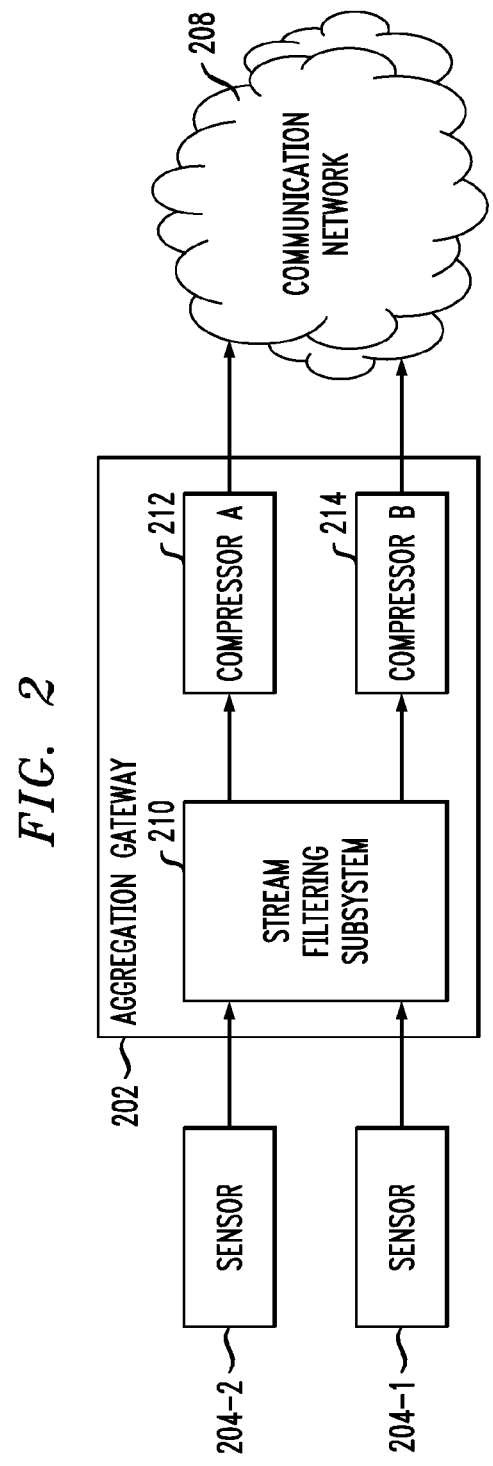
FIG. 2 is a diagram illustrates an aggregation gateway of the data collection system, according to an embodiment of the present invention.

Referring now to FIG. 2, a diagram illustrates an aggregation gateway of the data collection system, according to an embodiment of the present invention. Aggregation gateway 202 is again in communication with a plurality of sensors 204-1, 204-2, as well as a communication network 208. Raw data is received from the plurality of sensors 204-1, 204-2 at a stream filtering subsystem 210 of aggregation gateway 202. Within aggregation gateway 202, processed data is transferred from stream filtering subsystem 210 to compressor A 212 and compressor B 214. FIG. 2 also illustrates that processed data from sensor 204-1 is transferred to compressor A 212, and processed data from sensor 204-2 is transferred to compressor B 214. The compressed data from compressor A 212 and compressor B 214 are sent to communication network 208.

Figure 3:
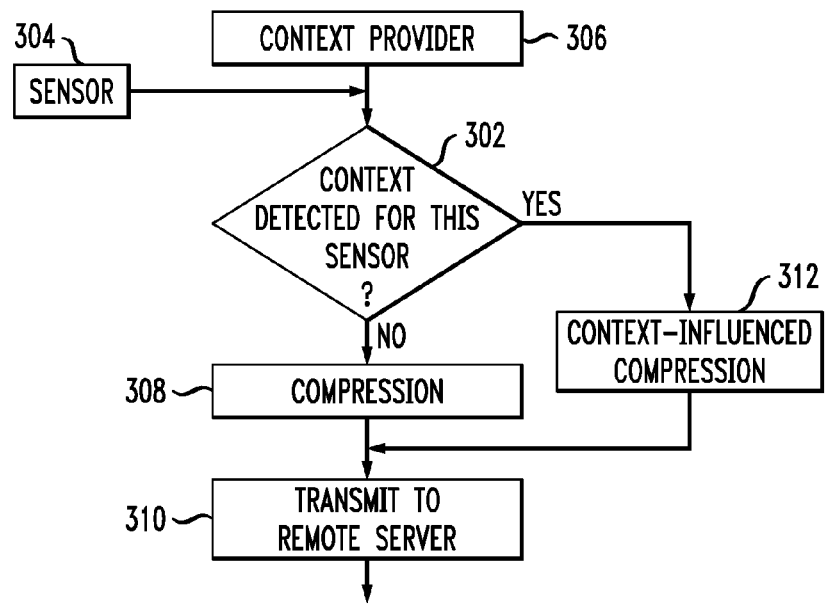
FIG. 3 is a flow diagram illustrating a compression adaptation methodology for the aggregation gateway of FIG. 2, according to an embodiment of the present invention.

Referring now to FIG. 3, a flow diagram illustrates a compression adaptation methodology for the aggregation gateway of FIG. 2, according to an embodiment of the present invention. In block 302, it is determined if a change in the context that is applicable for the processing and transport of data from a specified sensor, based on input from sensor 304, aggregation gateway 202 and context provider 306. Context may include for example, the location of the sensor, the degree of accuracy required of the sensor data, or the range of sensor data to be monitored, the medical conditions being diagnosed, the battery level of the gateway device or the quality of the gateway device's network connections. In the example presented in FIG. 3, the client device becomes aware of this change directly. If context is not detected in block 302, the data is compressed in block 308. If context is detected in block 302, the compression algorithm used in the compression block for the stream is updated and the sensor data is now compressed in accordance with the updated compression algorithm. This is referred to as context-influenced compression in block 312. Compressed data (either from block 308 or 312) is transmitted to a remote server in block 310. The client device or sensor determines the new type of event processing that it must invoke on the sensor data stream and the compression method that it must invoke on the subsequent processed output stream, and then switches to this new filtering and compression technique, such that all subsequent samples of the sensor data stream are now processed using this newly instantiated technique.

The form of compression used on the sensor data may be either lossless or lossy, and can even include, as a special case, uncompressed (raw) transmission of the data. Further, the modification to the compression procedure can include the modification of one or more parameters, such as, for example, the target SNR or level of fidelity, of the prior compression scheme already in use. Moreover, the change in the compression scheme can apply to one or more streams of sensor data, such as, for example, a change in the location from "gym" to "home" may imply the switch to a lossy VQ-based compressor for the ECG data as well as the switch to a coarser-resolution ("smaller codebook") quantizer associated with an entropy coder for the accelerometer data. Additionally, the compressor itself may operate not just independently on each individual sensor data stream, but may also perform joint compression. For example, the compressor may perform a joint VQ on accelerometer and body temperature sensor readings. Similarly, the event processing applied on the sensor data can involve simply the direct transmission of the raw sensor events or the processing of these events in various ways (e.g., generating statistical summaries, threshold-based filtering to eliminate samples within specific ranges or applying spatio-temporal operators to extract higher level features from the raw sensor data).

Figure 4:
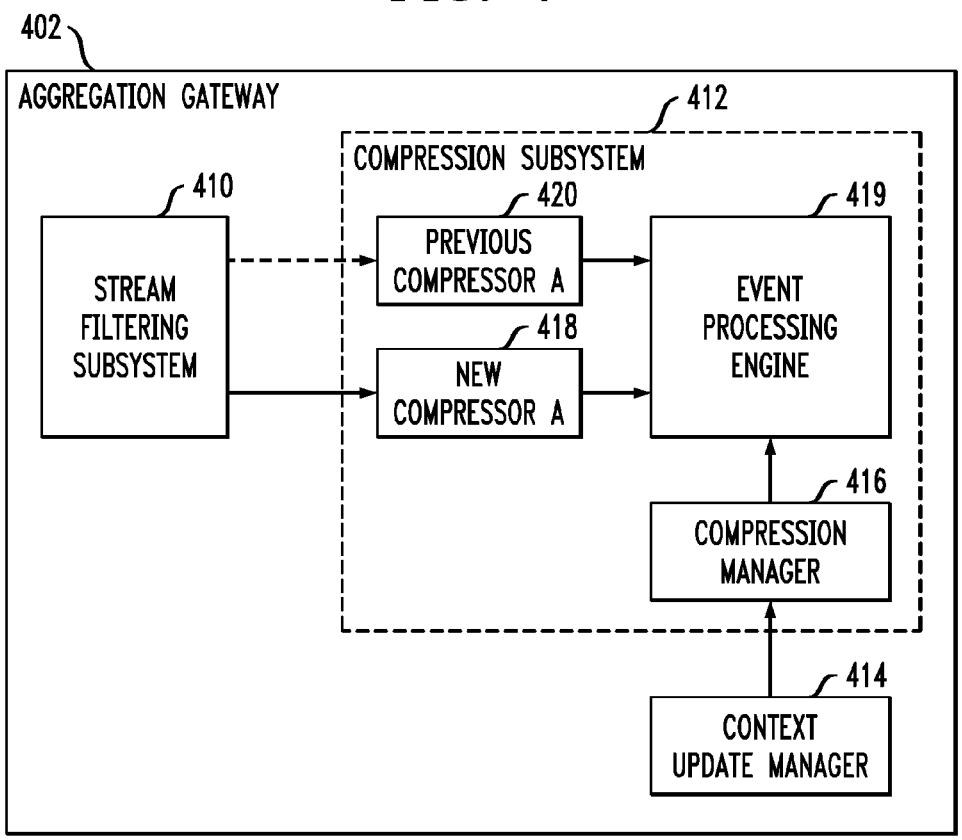
FIG. 4 is a diagram illustrating an aggregation gateway of the data collection system, according to another embodiment of the present invention.

Referring now to FIG. 4, a diagram illustrates an aggregation gateway of the data collection system, according to another embodiment of the present invention. A stream filtering subsystem 410 of aggregation gateway 402 receives sensor data. Processed data is sent from stream filtering subsystem 410 to a compression subsystem 412. A context update manager 414 receives a modification demand from a server, indicating the need for a change in either the individual compression algorithm or the event processing logic or both. Context update manager 414 is in communication with a compression manager 416 of compression subsystem and the event processing engine 419 of the event subsystem, so that, for example, processed data may be compressed by a new compressor A' 418 instead of its previous compressor A 420.

Figure 5:
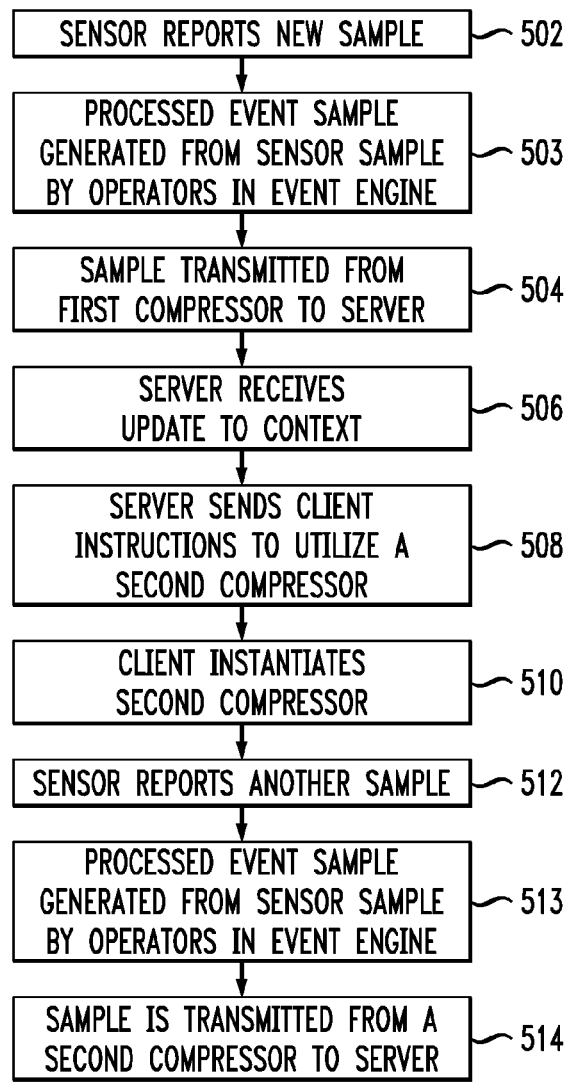
FIG. 5 is a flow diagram illustrating a compression adaptation methodology for the aggregation gateway of FIG. 4, according to an embodiment of the present invention.

Referring now to FIG. 5, a flow diagram illustrates a compression adaptation methodology for the aggregation gateway of FIG. 4, according to an embodiment of the present invention. In block 502, a sensor reports a new sample. This sample is then fed as an input to an event processing engine 503, consisting of one or more event operators that process the input stream of sensor data to generate an output stream of events. In block 504, the compressed version of the event samples output by the event processing engine 503 is transmitted from a first compressor to the server. In block 506, the server receives an update to context. An update to context may include for example, a location of the sensor, a change in the medical anomalies being investigated, the addition of a new prescription drug for the user of the gateway device, a modification in the degree of accuracy required of the sensor data, or the range of sensor data to be monitored. In block 508, the server sends the client instructions to utilize a second alternative compressor (and perhaps, a change in the event processing rules). In block 510, the client instantiates the second compressor. In block 512, the sensor reports another sample, which is then processed as before by the event processing engine 513 (based on the previous unmodified or newly modified processing rules) and in block 514, the compressed version of the new events generated by the event processing engine is transmitted from a second compressor to the server.

The notification of the change in external context may be achieved by having the remote infrastructure explicitly communicate the new context, or transmit a new rule, or index to a previously stored rule, to implicitly indicate the modification in the compression technique.

The selection of the specific new compression technique to be invoked on the device may be done in several ways. One approach may to be to store a table of various compression techniques, as well as the actual compressor executable code, on the device, and have a predicate specifying what contextual conditions trigger the selection of a specific entry in the table. Alternately, the remote infrastructure could dynamically download the index of the entry in the table to be invoked based on the most recent context. Finally, the remote infrastructure could dynamically download the compressor code itself (in compiled or pre-compiled form) to the client device or sensor, which could then instantiate this new executable and redirect subsequent samples of the sensor data stream to this new compressor.

Figure 6:
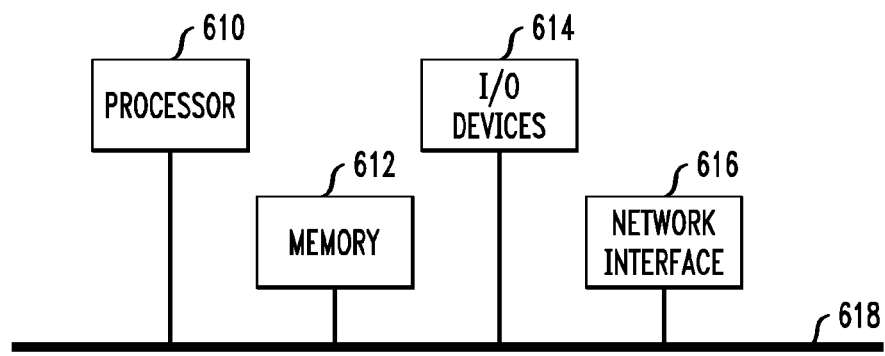
FIG. 6 is a block diagram illustrating an exemplary hardware implementation of a computing system in accordance with which one or more components/methodologies of the invention may be implemented, according to an embodiment of the present invention.

Referring now to FIG. 6, a block diagram illustrates an exemplary hardware implementation of a computing system in accordance with which one or more components/methodologies of the invention (e.g., components/methodologies described in the context of FIGS. 1-5) may be implemented, according to an embodiment of the present invention.

As shown, the computer system may be implemented in accordance with a processor 610, a memory 612, I/O devices 614, and a network interface 616, coupled via a computer bus 618 or alternate connection arrangement.

It is to be appreciated that the term "processor" as used herein is intended to include any processing device, such as, for example, one that includes a CPU (central processing unit) and/or other processing circuitry. It is also to be understood that the term "processor" may refer to more than one processing device and that various elements associated with a processing device may be shared by other processing devices.

The term "memory" as used herein is intended to include memory associated with a processor or CPU, such as, for example, RAM, ROM, a fixed memory device (e.g., hard drive), a removable memory device (e.g., diskette), flash memory, etc.

In addition, the phrase "input/output devices" or "I/O devices" as used herein is intended to include, for example, one or more input devices (e.g., keyboard, mouse, scanner, etc.) for entering data to the processing unit, and/or one or more output devices (e.g., speaker, display, printer, etc.) for presenting results associated with the processing unit.

Still further, the phrase "network interface" as used herein is intended to include, for example, one or more transceivers to permit the computer system to communicate with another computer system via an appropriate communications protocol.

Software components including instructions or code for performing the methodologies described herein may be stored in one or more of the associated memory devices (e.g., ROM, fixed or removable memory) and, when ready to be utilized, loaded in part or in whole (e.g., into RAM) and executed by a CPU.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for changing or modifying the compression technique employed by a client device transmitting a data stream to a server of a data collection system, the method comprising the steps of:

detecting at least one change to at least one contextual condition of a user of the client device, wherein the at least one contextual condition of the user of the client device comprises one of a location of the user and an activity of the user;

selecting a different compression technique or modifying the parameters of the currently instantiated compression technique in response to the at least one change to the at least one contextual condition of the user of the client device, wherein the compression technique selected is a lossless compression algorithm when the at least one change to the at least one contextual condition of the user of the client device implies at least a desirability for transmission of accurate data, and a lossy compression algorithm when the at least one change to the at least one contextual condition of the user of the client device implies at least a desirability for transmission of less than accurate data; and altering the currently instantiated compression technique of at least one client device in accordance with the one or more modifications to form a modified compression technique through which the data stream will be compressed before being sent to a server of the data collection system.

2. The method of claim 1, wherein the steps of detecting at least one change and generating one or more modifications are performed at the server of the data collection system.

3. The method of claim 2, further comprising the step of transmitting the one or more modifications from the server to the at least one client device.

4. The method of claim 1, further comprising the steps of:
    compressing the data stream in accordance with the defined compression technique at the at least one client device; and
    transmitting the compressed data stream from the at least one client device to the server.

5. The method of claim 1, further comprising the steps of:
    selecting the different compression technique in conjunction with modifying a set of sensor event processing operations currently instantiated on the client device; and
    jointly altering the currently instantiated event processing operators and the compression technique applied on one or more sensor streams of at least one client device.

6. The method of claim 1, further comprising the steps of:
    compressing the data stream in accordance with the modified compression technique at the at least one client device; and
    transmitting the compressed data stream from the at least one client device to the server.

7. The method of claim 6, wherein, in the step of transmitting the compressed data stream, the compressed data stream transmitted to the server comprises compressed versions of one or more data samples or compressed versions of one or more processed events generated by the application of event processing operators applied to one or more data samples.

8. The method of claim 6, wherein, in the step of transmitting the compressed data stream, the compressed data stream transmitted to the server comprises compressed versions of statistical parameters or higher-level features generated from one or more data samples.

9. The method of claim 1, wherein the step of detecting at least one change to at least one contextual condition of the user of the client device comprises the step of determining the at least one contextual condition of the user of the client device from at least a portion of data received from the client device.

10. The method of claim 1, wherein the step of detecting at least one change to at least one contextual condition of the user of the client device comprises the step of determining the at least one contextual condition of the user of the client device from at least one of an attribute of the at least one client device and at least one user of the at least one client device.

11. The method of claim 1, wherein, in the step of generating one or more modifications, the one or more modifications comprise a command to at least one of modify, activate and deactivate one or more compression techniques stored a-priori at the at least one client device.

12. The method of claim 1, wherein, in the step of generating one or more modifications, the modifications comprise context data that invokes a stored compression technique stored a-priori at the at least one client device.

13. The method of claim 1, wherein, in the step of generating one or more modifications, the modifications comprise at least one of code and logic of a compression technique to be invoked at the at least one client device.

14. The method of claim 1, wherein the step of altering the compression technique further comprises the step of modifying one or more parameters of at least one currently instantiated compression technique on the at least one client device.

15. The method of claim 1, wherein the step of altering the compression technique further comprises the step of operating at least one currently instantiated compression technique on a different set of data streams.

16. The method of claim 1, wherein the modified compression technique causes the data stream to be transmitted with a different level of data quality than the currently instantiated compression technique.

17. An article of manufacture for modifying a compression technique employed over a data stream in a data collection system, the article comprising a non-transitory computer readable storage medium having tangibly embodied thereon computer readable instructions which, when executed, cause one or more processors to:
    detect at least one change to at least one contextual condition of the user of the client device, wherein the at least one contextual condition of the user of the client device comprises one of a location of the user and an activity of the user;
    generate one or more modifications to a defined compression technique in response to the at least one change to the at least one contextual condition of the user of the client device, wherein the compression technique is a lossless compression algorithm when the at least one change to the at least one contextual condition of the user of the client device implies at least a desirability for transmission of accurate data, and a lossy compression algorithm when the at least one change to the at least one contextual condition of the user of the client device implies at least a desirability for transmission of less than accurate data; and alter the defined compression technique of at least one client device in accordance with the one or more modifications to form a modified compression technique through which the data stream will be compressed before being sent to a server of the data collection system.

18. An apparatus for modifying a compression technique employed over a data stream in data collection system, comprising:

a memory; and at least one hardware processor coupled to the memory and operative to: (i) detect at least one change to at least one contextual condition of the user of the client device, wherein the at least one contextual condition of the user of the client device comprises one of a location of the user and an activity of the user, (ii) generate one or more modifications to a defined compression technique in response to the at least one change to the at least one contextual condition of the user of the client device, wherein the compression technique is a lossless compression algorithm when the at least one change to the at least one contextual condition of the user of the client device implies at least a desirability for transmission of accurate data, and a lossy compression algorithm when the at least one change to the at least one contextual condition of the user of the client device implies at least a desirability for transmission of less than accurate data, and (iii) transmit the one or more modifications to at least one client device of the data collection system.

19. An apparatus for modifying a compression technique employed over a data stream in data collection system, comprising:

a memory; and at least one hardware processor coupled to the memory and operative to: (i) receive one or more modifications from a server of the data collection system; and (ii) alter a defined compression technique in accordance with the one or more modifications to form a modified compression technique through which the data stream will be compressed before being sent to the server, wherein the one or more modifications are determined based on a change to at least one contextual condition of a user of a client device sending the data stream, wherein the at least one contextual condition comprises one of a location of the user and an activity of the user, and wherein the modified compression technique is a lossless compression algorithm when the at least one change to the at least one contextual condition of the user of the client device implies at least a desirability for transmission of accurate data, and a lossy compression algorithm when the at least one change to the at least one contextual condition of the user of the client device implies at least a desirability for transmission of less than accurate data.

\* \* \* \* \*